United States Patent [19]

Bauman et al.

[11] 4,265,810

[45] May 5, 1981

[54] PROCESS FOR RECOVERING ZWITTERIONIC DIAZONIUM SALTS BY AGGREGATION

[75] Inventors: Donald L. Bauman, Wilmington, Del.; Masuo Toji, Barnsboro, N.J.

[73] Assignee: E. I. Du Pont de Nemours and Company, Wilmington, Del.

[21] Appl. No.: 157,002

[22] Filed: Jun. 6, 1980

Related U.S. Application Data

[63] Continuation-in-part of Ser. No. 954,824, Oct. 26, 1978, abandoned.

[51] Int. Cl.³ .......................................... C07C 113/04
[52] U.S. Cl. .................. 260/141; 260/404.5; 260/451 A; 548/354; 564/291; 564/292; 564/282; 564/288
[58] Field of Search ............................... 260/141 PS

[56] References Cited

U.S. PATENT DOCUMENTS

| | | | |
|---|---|---|---|
| 2,812,321 | 11/1957 | Eberhart et al. | 260/141 S X |
| 2,845,326 | 7/1958 | Streck | 260/141 P |

FOREIGN PATENT DOCUMENTS

| | | | |
|---|---|---|---|
| 574556 | 4/1959 | Canada | 260/141 P |
| 37-9574 | 7/1962 | Japan | 260/141 P |
| 1072702 | 6/1967 | United Kingdom | 260/141 P |

*Primary Examiner*—Floyd D. Higel

[57] ABSTRACT

Zwitterionic diazonium salts, derived from aromatic amines, are aggregated by: (a) diazotizing said amine to a zwitterionic diazonium salt in the presence of a cationic surfactant or (b) diazotizing said amine and thereafter treating the resulting zwitterionic diazonium salt with a cationic surfactant, so as to give particles of the diazonium salts which are readily separable from the liquid mass in which they are formed.

22 Claims, No Drawings

PROCESS FOR RECOVERING ZWITTERIONIC DIAZONIUM SALTS BY AGGREGATION

CROSS REFERENCE TO RELATED APPLICATION

This is a continuation-in-part of application Ser. No. 954,824, filed Oct. 26, 1978, now abandoned.

BACKGROUND OF THE INVENTION

This invention relates to a process for recovering zwitterionic diazonium salts, derived from aromatic amines, which comprises: (a) diazotizing said amine to a zwitterionic diazonium salt in the presence of a cationic surfactant or (b) diazotizing said amine and thereafter treating the resulting zwitterionic diazonium salt with a cationic surfactant. The presence of the cationic surfactant during or after diazotization causes the zwitterionic aromatic diazonium salt to aggregate so as to give particles thereof which are readily separable from the liquid mass in which they are formed.

Amines can be diazotized by the use of several techniques. In the direct diazotization process, an acidic slurry of the amine is prepared and a nitrite is added thereto. In the so-called reverse method, the amine is dissolved in alkali, a soluble nitrite is added, and that mixture is poured into an acid, such as hydrochloric acid, so as to effect the diazotization. Various difficulties have been encountered with both methods. For example, in the diazotization of an aminosulfonic acid by the direct method, incomplete diazotization is often encountered if the aminosulfonic acid is not freshly precipitated in a finely divided state. While the reverse method usually results in complete diazotization of an aminosulfonic acid, the resulting insoluble zwitterionic diazonium salt is often formed in such a finely divided state that it is difficult to isolate. The process of the present invention provides for complete diazotization and results in the diazonium salt being in such a state of aggregation that it is readily separable from the liquid components in which it is formed.

In U.S. Pat. No. 2,845,326, a stable dispersion of a diazotizable primary amine devoid of solubilizing groups e.g. OH or $SO_3H$, is obtained by the combined use of a cationic compound and non-ionic compound.

In U.S. Pat. No. 2,812,321, it is disclosed that the addition of a surface-active agent of the polyoxyethylene fatty ester class to the 1,2,4-acid diazotization reaction mixture causes it to remain fluid throughout the diazotization process.

U.K. Patent Specification No. 1,072,702 discloses a process for producing a pigment having improved flow properties, dispersibility or gloss retention properties which comprises precipitating the pigment in the presence of two surfactants, or after-treating a slurry of the pigment with two surfactants, one of the surfactants being cationic and the other surfactant being anionic in character, and both surfactants having a surface tension of not more than 38.5 dynes per cm in a 0.2% by weight aqueous solution at 25° C.

DETAILED DESCRIPTION OF THE INVENTION

By definition a zwitterionic diazonium compound is one containing a substituent that functions as an anion. Common examples of such substituents in the dye art are the sulfonic acid group and the hydroxyl group. This invention relates to the disclosed processing of diazotizable aromatic amines which, because of their proton donor content, are zwitterionic. It relates particularly to such processing of diazotizable aromatic amines having OH or $SO_3H$ substituents, for example, dehydrothio-p-toluidine sulfonic acid (DHTPTSA) having the formula:

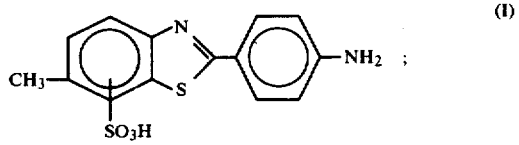

(I)

2-aminobenzothiazole-6-sulfonic acid, having the formula:

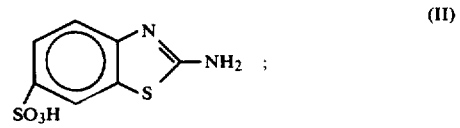

(II)

4-aminoazobenzene-4'-sulfonic acid having the formula:

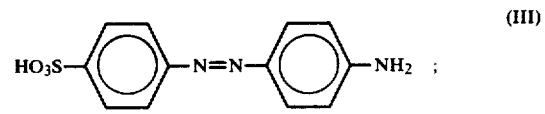

(III)

3-methoxy-4-aminoazobenzene-3'-sulfonic acid; and 2,5-dichloroaniline sulfonic acid.

The cationic surfactant must have at least one long chain ($C_{10}$–$C_{18}$) aliphatic substituent. The best cationic agents have two long chains ($C_{16}$–$C_{18}$) aliphatic substituents. In particular, the cationic surfactants are (1) ammonium compounds of the formula:

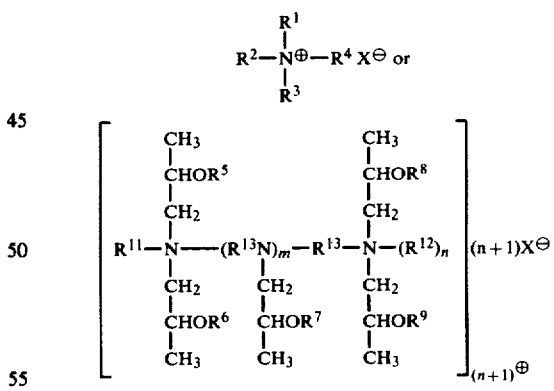

wherein $R^1$–$R^4$ are alkyl containing 1–18 carbons, alkenyl containing 8–18 carbons, or benzyl; at least one of $R^1$–$R^4$ is a $C_{10}$–$C_{18}$ alkyl or alkenyl; preferably two of $R^1$–$R^4$ are $C_{16}$–$C_{18}$ alkyl or alkenyl; provided that no more than one of $R^1$–$R^4$ is benzyl;

$R^5$–$R^9$ are hydrogen or $R^{10}CO$—, at least two thereof being $R^{10}CO$—;

$R^{10}$ is alkyl or alkenyl containing 11–17 carbons;

$R^{11}$ and $R^{12}$ are $C_1$–$C_4$ alkyl;

$R^{13}$ is a bivalent alkylene having 2 to 6 carbons;

m is 0 to 2;

n is 0 or 1; and $X^{\ominus}$ an anion; or (2) imidazolium compounds of the formula:

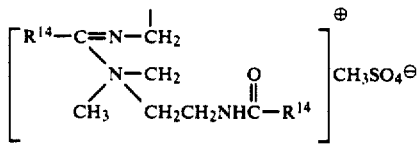

wherein $R^{14}$ is $C_{15}-C_{17}$ aliphatic chain.

The amount of the cationic adjuvant may vary from one diazonium salt to another. One would use the minimum amount required to effect the degree of aggregation desired. That effect can be determined by observation. Generally, one would use between 0.5 and 5 weight % of the cationic compound, based upon the weight of diazonium compound.

The process of this invention can be applied to diazotizations by the direct or the reverse method. Moreover, the cationic surfactant may be present in the reaction mixture during diazotization or it can be added thereto after completion of the diazotization step.

For example, dehydrothio-p-toluidine sulfonic acid (DHTPTSA) is slurried or dissolved in a slight excess of aqueous alkali. The alkali can be sodium hydroxide, potassium hydroxide, or lithium hydroxide. A mixture of potassium and lithium hydroxide is preferred to form a stable solution of DHTPTS. The lithium-potassium DHTPTS solution is drowned in hydrochloric acid. Aqueous sodium nitrite is added. After destroying the excess nitrite, a cationic adjuvant is added to aggregate the diazo into a filterable form. It may be helpful to digest the diazo at 30°-60° C. to further improve the physical form. The diazo is isolated by filtration, washed with water, slurried in water, and then coupled with a coupler using a base such as triethanolamine. The cationic adjuvant can be removed by filtration of the liquid.

The following examples further illustrate the invention.

EXAMPLE 1

The adjuvants shown below have been evaluated in the DHTPTSA process described above. After the diazotization was completed, the cationic adjuvant was added in a quantity equivalent to 1.57% by weight, based on the weight of DHTPTSA, and the resulting mixture was held at 32° C. for one hour. The filter leaf test was then performed on the mixture.

The filter leaf test involves the use of a filter dip disc (3.4 cm dia.) on which a vacuum can be drawn. The filter dip disc was put into the diazo slurry for 10 sec. (pick up), withdrawn, and allowed to dewater for 10 sec. The diazo collected was weighed, dried, and weighed again. The volume of the filtrate was measured. In another series of tests, the diazo was digested at 50° C. for one hour and the filter leaf tests run at 50° C. The control run contained no adjuvant.

| Trade Name | Chemical Name |
|---|---|
| "Avitex" ML | A quaternary ammonium compound represented by the formula: [CH₃CH(OR)CH₂]₂NCH₂CH₂— [CH₂CH(OR)CH₃]₂ wherein about |
| | two of the R groups are hydrogen and about two thereof are oleyl |
| Adogen 442 | Di(hydrogenated tallow)dimethyl ammonium chloride |
| Adogen 471 | Tallow trimethyl ammonium chloride |
| Adogen 477 | N-tallow-pentamethyl propane diammonium dichloride |
| Variquot 60LC | Dimethylalkyl ($C_{10}-C_{18}$) benzyl ammonium chloride |
| Variquot K75 | Methyl (1) soya amidoethyl (2) soya imidazolium methyl sulfate |
| Varisoft 3690 | Methyl (1) oleylamidoethyl (2) oleyl imidazolium methyl sulfate |
| BTEAc | Benzyl triethyl ammonium chloride |
| TBAc | Tetrabutyl ammonium chloride |

| | Filter Leaf Tests (10 Sec. Pick-Up 10 Sec. Dewater) | | | | | |
|---|---|---|---|---|---|---|
| | 32° C. | | | 50° C. | | |
| Adjuvant | Wt. | Dry Wt. | ml/ Filtrate | Wt. | Dry Wt. | ml/ Filtrate |
| Control | 8 | 4 | 20 | 13 | 6 | 30 |
| BTEAc | 8 | 4 | 21 | 12 | 6 | 29 |
| TBAc | 8 | 4 | 22 | 11 | 5 | 25 |
| "Avitex" ML | 10 | 5 | 26 | 22 | 10 | 50 |
| Adogen 442 | 12 | 6 | 33 | 17 | 9 | 50 |
| Adogen 471 | 9 | 4 | 19 | 11 | 5 | 26 |
| Adogen 477 | 9 | 4 | 21 | 12 | 5 | 28 |
| Variquot 60LC | 11 | 5 | 22 | 15 | 7 | 34 |
| Variquot K75 | 13 | 6 | 29 | 22 | 10 | 48 |
| Varisoft 3690 | 13 | 6 | 30 | 19 | 9 | 47 |

At the concentration used in the tests, all of the foregoing except Adogen 471, BTEAc and TBAc were found to have some beneficial effect on the diazonium salt. "Avitex" ML, Adogen 442, Variquot 60LC, Variquot K75, and Varisoft 3690 were found to be particularly effective.

EXAMPLES 2–4

The procedure of Example 1 was repeated to give the following results:

| | Filter leaf tests Wet cake(g) | 10 sec pick up ml filtrate | 10 sec dewater dry cake(g) |
|---|---|---|---|
| | 4-Aminoazobenzene-4'-sulfonic acid | | |
| Control (26° C.) | 5.3 | 33 | 2.4 |
| Variquot K75 | 6.3 | 39 | 3.0 |
| Variquot K75 (40° C.) | 6.7 | 46 | 3.4 |
| | 2,5-Dichloroaniline sulfonic acid | | |
| Control (15° C.) | 1.9 | 66 | 1.0 |
| Variquot K75 (15° C.) | 1.1 | 32 | 0.5 |
| Variquot K75 (35° C.) | 2.2 | 90 | 1.4 |
| | 3-Methoxy-4-aminoazobenzene-3'-sulfonic acid | | |
| Control (25° C.) | 15.0 | 58 | 9.0 |
| Variquot K75 | 19.0 | 86 | 11.8 |

EXAMPLES 5 AND 6

An aqueous hydrochloric acid slurry of 4-aminoazobenzene-4'-sodium sulfonate (AABSS) was diazotized in a control run as follows:

To 380 ml of water were added 70 g of 31.5% HCl and 95 g of 60% AABSS. That mixture was cooled to 15° C., then its temperature was allowed to rise at will. Over a period of 1 hour, 36 g of 40% sodium nitrite were added, and thereafter the mixture was held for 1 hour. At the end of that 1-hour period, 12 g of 15% sulfamic acid were added over a period of 30 minutes, and the mixture was held for another 10 minutes so as to destroy the excess sodium nitrite.

The foregoing diazotization reaction was repeated for Examples 5 and 6; however, after the HCl had been added and before addition of the AABSS, a cationic surfactant was added to the reaction mixture. In the case of Example 5, 4 g of Avitex ML were added, and in the case of Example 6, 4 g of Avitex Y were added. Avitex Y is the reaction product of diethylenetriamine, propylene oxide, stearic acid and methyl sulfate having an average structure represented by the formula:

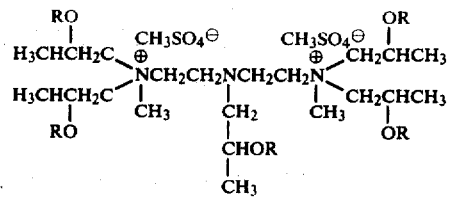

wherein about two of R are hydrogen and the remainder thereof are stearyl.

In a filter leaf test for the reaction masses obtained for the Control and for Examples 5 and 6, the rate of filtration and washing were judged by the volume of filtrate collected after specific filtration and washing times, as recited below. The filtration and washing tests were performed using a one-square-inch filter leaf connected to a vacuum source (when deadheaded, the source would provide a vacuum of 21 inches of mercury).

The following data show that Avitex ML and Avitex Y can increase the rate of filtration, and more importantly, washing of the diazonium zwitterion resulting from the diazotization of AABSS.

| Pickup Time (sec) | Wash Time (sec) | Dewater (sec) | Filtrate (ml) Control | Ex. 5 | Ex. 6 |
|---|---|---|---|---|---|
| 5 | — | 20 | 2.5 | 7.5 | 7.8 |
| 10 | — | 20 | 7.8 | 15.5 | 15.5 |
| 5 | 10 | 20 | 9.0 | 16.0 | 17.5 |
| 5 | 20 | 20 | 10.5 | 24.0 | 23.0 |
| 5 | 40 | 20 | 17.5 | 37.0 | 32.5 |

EXAMPLES 7-9

In a control diazotization process, 63.3 g of a sulfonation mass containing 0.07 mole of 2-aminobenzothiazole-6-sulfonic acid (prepared by reacting 2-aminobenzothiazole with 98% $H_2SO_4$ for about 2 hours at about 120° C.), 15 g of acetic acid, 45 ml of water and 24.2 g of a 38.4% solution of nitrosyl sulfuric acid (0.073 mole) were reacted at 25° C. for 1½ hours. In the diazotization processes of Examples 7, 8 and 9, 0.8 g of a surfactant was added before addition of the nitrosyl sulfuric acid. The control mass and those for Examples 7, 8 and 9 were filtered on a sintered glass funnel under a vacuum of about 125 mm of Hg. The volume of filtrate which was collected in 12 minutes is recorded below.

| Example | Filtrate (ml) |
|---|---|
| 7 - Avitex ML | 32.5 |
| 8 - Varisoft 3690 | 54.5 |
| 9 - Variquot 60LC | 28.5 |
| No surfactant | 15 |

We claim:

1. A process for recovering solid zwitterionic diazonium salts derived from diazotizable aromatic amines capable of forming zwitterionic diazonium salts which consists essentially in:
   (a) diazotizing said amine to a zwitterionic diazonium salt in the presence of a cationic surfactant or
   (b) diazotizing said amine and thereafter treating the resulting zwitterionic diazonium salt with a cationic surfactant, said cationic surfactant being
   (1) an ammonium compound of the formula:

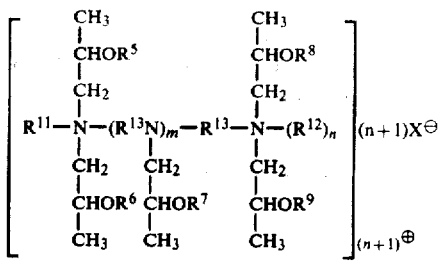

wherein
$R^1$-$R^4$ are alkyl containing 1-18 carbons, alkenyl containing 8-18 carbons, or benzyl; at least one of $R^1$-$R^4$ is a $C_{10}$-$C_{18}$ alkyl or alkenyl; provided that no more than one of $R^1$-$R^4$ is benzyl;
$R^5$-$R^9$ are hydrogen or $R^{10}CO$—, at least two thereof being $R^{10}CO$—;
$R^{10}$ is alkyl or alkenyl containing 11-17 carbons;
$R^{11}$ and $R^{12}$ are $C_1$-$C_4$ alkyl;
$R^{13}$ is a bivalent alkylene having 2 to 6 carbons;
m is 0 to 2;
n is 0 or 1; and
$X^\ominus$ an anion; or
(2) imidazolium compounds of the formula:

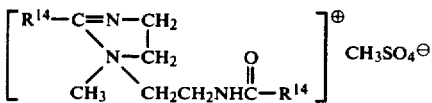

wherein $R^{14}$ is a $C_{15}$-$C_{17}$ aliphatic hydrocarbon.

2. The process of claim 1 wherein said amine is dehydrothio-p-toluidine sulfonic acid.

3. The process of claim 1 wherein said amine is 2-aminobenzothiazole-6-sulfonic acid.

4. The process of claim 1 wherein said amine is 4-aminoazobenzene-4'-sulfonic acid.

5. The process of claim 1 wherein said amine is 2,5-dichloroaniline sulfonic acid.

6. The process of claim 1 wherein said amine is 3-methoxy-4-aminoazobenzene-3'-sulfonic acid.

7. The process of claim 1, 2, 3, 4, 5 or 6 wherein said diazotization is carried out in the presence of said cationic surfactant.

8. The process of claim 1, 2, 3, 4, 5 or 6 wherein said amine is first diazotized and thereafter treated with said cationic surfactant.

9. The process of claim 1 wherein two of $R^1$–$R^4$ are $C_{16}$–$C_{18}$ alkyl or alkenyl.

10. The process of claim 9 wherein said amine is dehydrothio-p-toluidine sulfonic acid.

11. The process of claim 9 wherein said amine is 2-aminobenzothiazole-6-sulfonic acid.

12. The process of claim 9 wherein said amine is 4-aminoazobenzene-4'-sulfonic acid.

13. The process of claim 9 wherein said amine is 2,5-dichloroaniline sulfonic acid.

14. The process of claim 9 wherein said amine is 3-methoxy-4-aminoazobenzene-3'-sulfonic acid.

15. The process of claim 9, 10, 11, 12, 13 or 14 wherein said diazotization is carried out in the presence of said cationic surfactant.

16. The process of claim 9, 10, 11, 12, 13 or 14 wherein said amine is first diazotized and thereafter treated with said cationic surfactant.

17. The process of claim 1, 2, 3, 4, 5 or 6 wherein said surfactant is a quaternary ammonium compound represented by the formula:

[CH$_3$CH(OR)CH$_2$]$_2$NCH$_2$CH$_2$N[CH$_2$CH(OR)CH$_3$]$_2$ wherein about two of the R groups are hydrogen and about two thereof are oleyl.

18. The process of claim 1, 2, 3, 4, 5 or 6 wherein said surfactant is di(hydrogenated tallow)dimethyl ammonium chloride.

19. The process of claim 1, 2, 3, 4, 5 or 6 wherein said surfactant is dimethylalkyl ($C_{10}$–$C_{18}$) benzyl ammonium chloride.

20. The process of claim 1, 2, 3, 4, 5 or 6 wherein said surfactant is methyl (1) soya amidoethyl (2) soya imidazolium methyl sulfate.

21. The process of claim 1, 2, 3, 4, 5 or 6 wherein said surfactant is methyl (1) oleylamidoethyl (2) oleyl imidazolium methyl sulfate.

22. The process of claim 1, 2, 3, 4, 5 or 6 wherein said surfactant is a compound represented by the formula:

$$\begin{array}{c}
\text{RO} \quad\quad\quad\quad\quad\quad\quad\quad\quad\quad\quad \text{OR} \\
| \quad\quad \text{CH}_3\text{SO}_4^\ominus \quad\quad \text{CH}_3\text{SO}_4^\ominus \quad | \\
\text{H}_3\text{CHCH}_2\text{C} \diagdown \underset{\oplus}{} \quad\quad\quad\quad\quad\quad \underset{\oplus}{} \diagup \text{CH}_2\text{CHCH}_3 \\
\diagup \text{NCH}_2\text{CH}_2\text{NCH}_2\text{CH}_2\text{N} \diagdown \\
\text{H}_3\text{CHCH}_2\text{C} \quad | \quad\quad\quad | \quad\quad\quad | \quad \text{CH}_2\text{CHCH}_3 \\
| \quad\quad \text{CH}_3 \quad\quad \text{CH}_2 \quad\quad \text{CH}_3 \quad | \\
\text{RO} \quad\quad\quad\quad\quad\quad | \quad\quad\quad\quad\quad\quad \text{OR} \\
\quad\quad\quad\quad\quad\quad \text{CHOR} \\
\quad\quad\quad\quad\quad\quad | \\
\quad\quad\quad\quad\quad\quad \text{CH}_3
\end{array}$$

wherein about two of R are hydrogen and the remainder thereof are stearyl.

* * * * *